United States Patent [19]
Konwitz

[11] Patent Number: 5,772,658
[45] Date of Patent: Jun. 30, 1998

[54] SIDE-EMITTING OPTICAL FIBERS FOR LASERS

[75] Inventor: Ellie Konwitz, Ramat Gan, Israel

[73] Assignee: Laser Industries, Ltd., Tel Aviv, Israel

[21] Appl. No.: 574,552

[22] Filed: Dec. 19, 1995

[30] Foreign Application Priority Data

Dec. 20, 1994 [IL] Israel ........................................ 112087

[51] Int. Cl.⁶ ..................................................... A61N 5/06
[52] U.S. Cl. .................................. 606/15; 606/2; 606/10; 606/13; 606/17; 385/36; 385/38; 385/147; 385/902
[58] Field of Search .......................... 606/2–14; 128/897; 385/36, 38, 147, 902

[56] References Cited

U.S. PATENT DOCUMENTS

| | | |
|---|---|---|
| 4,740,047 | 4/1988 | Abe et al. ..................................... 606/2 |
| 5,246,436 | 9/1993 | Rowe . |
| 5,320,620 | 6/1994 | Long et al. . |
| 5,343,543 | 8/1994 | Novak ......................................... 385/31 |
| 5,366,456 | 11/1994 | Rink et al. ................................ 606/15 |
| 5,428,699 | 6/1995 | Pon . |
| 5,430,634 | 7/1995 | Baker et al. . |

*Primary Examiner*—David M. Shay
*Attorney, Agent, or Firm*—Cobrin Gittes & Samuel

[57] ABSTRACT

There is provided a side-emitting optical fiber having a proximal end for receiving radiation and a distal end for emitting the radiation in a direction laterally of the longitudinal axis of the fiber via a radiation exit region at the distal end; characterized in that the outer surface of the distal end of the a glass cap is formed with a visually discernible surface formation which is narrow at one end thereof and which increases in width towards the opposite end thereof, to thereby enable visually discerning the orientation of the optical fiber with respect to the radiation exit region thereof.

22 Claims, 2 Drawing Sheets

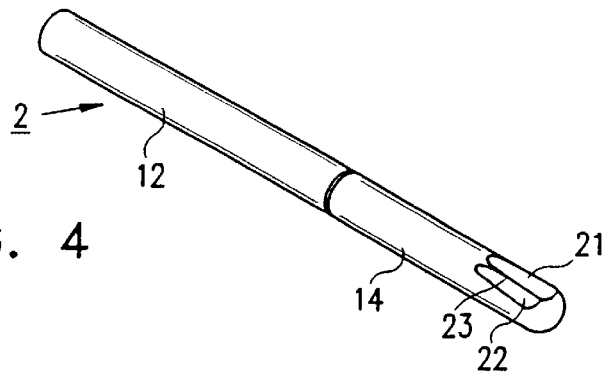
FIG. 4
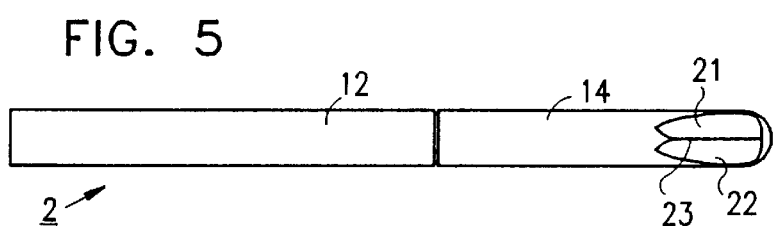
FIG. 5
FIG. 6
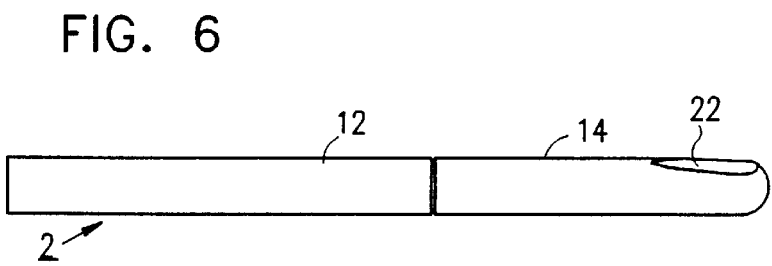
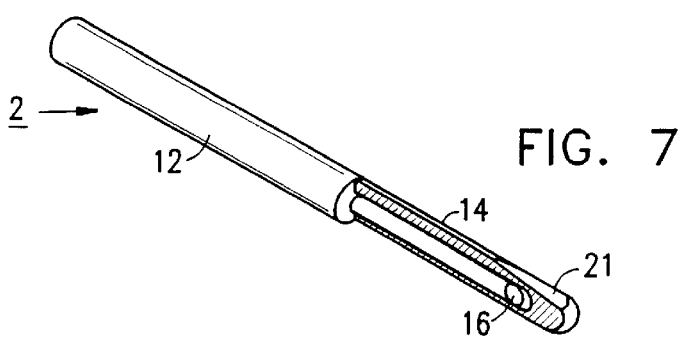
FIG. 7

SIDE-EMITTING OPTICAL FIBERS FOR LASERS

The present invention relates to side-emitting (or side-firing) optical fibers such as are used in laser surgery. The invention is particularly directed to an optical fiber construction which enables visually discerning the orientation of the optical fiber with respect to the radiation exit region thereof.

Laser apparatus used during an examination or surgery commonly include optical fibers for directing the laser radiation from the laser to the tissue being examined or treated. When end-firing fibers are used, i.e., wherein the laser radiation is emitted axially of the fiber end, the surgeon can easily discern the direction of the emitted radiation according to the axis of the emitting fiber. However, in side-emitting (side-firing) optical fibers, wherein the radiation is emitted laterally of the longitudinal axis of the fiber, the surgeon generally can discern the direction of the radiation emission only by observing the effects of the radiation since the radiation itself is generally not visible.

U.S. Pat. No. 5,343,543 describes one arrangement for enabling a surgeon to discern the direction of radiation emission from a side-fired optical fiber. The arrangement described in that patent includes a linear marking of ink formed as a plurality of spaced apart segments. As described in that patent, such linear ink markings not only permit determining the orientation of the radiation exit region of the fiber, but also permit measurement of the depth of insertion of the laser fiber into tissue, and measurements of tissue at the surgical site.

An object of the present invention is to provide a side-emitting optical fiber, particularly useful as a side-firing laser fiber, which also enables determining the orientation of the emitted radiation but which provides a number of advantages over the arrangement described in U.S. Pat. No. 5,343,543 as will be described more particularly below.

According to the present invention, there is provided a side-emitting optical fiber having a proximal end for receiving radiation and a distal end for emitting the radiation in a direction laterally of the longitudinal axis of the fiber via a radiation exit region at the distal end; characterized in that the outer surface of the distal end of the fiber is formed with a visually discernible surface formation which is narrow at one end thereof and which increases in width towards the opposite end thereof, to thereby enable visually discerning the orientation of the optical fiber with respect to the radiation exit region thereof.

According to further features in the described preferred embodiment, the visually discernible surface formation is narrow at the end facing the proximal end of the fiber, and increases in width towards the opposite end facing the outer tip of the distal end of the fiber. More particularly, the outer surface of the distal end of the fiber is substantially of cylindrical configuration and terminates in a substantially semi-spherical outer tip, and the visually discernible surface formation formed therein includes a substantially flattened surface extending at an acute angle to the longitudinal axis of the fiber from its outer tip to a point inwardly of its outer tip.

A side-emitting optical fiber constructed in accordance with the foregoing features provides a number of advantages particularly when used for laser surgery or for laser examination. Thus, this visually discernible surface formation formed on the outer surface of the fiber is permanent and not easily removable as ink markings. Since it is in the form of a permanent surface formation, it can be, and preferably is, formed on the outer surface of a glass cap covering the radiation-emitting end of the fiber. In addition, since this surface formation decreases in width from its outer tip inwardly of the fiber, and since its dimensions are known beforehand, this surface formation can be used not only to indicate the orientation of the radiation-emitting region of the fiber, but also to indicate the depth of penetration of the fiber into tissue, as well as to indicate the size of tissue at the working site of the fiber.

In one described embodiment, the visually discernible surface formation includes only a single such flattened surface. In a second described embodiment, it includes two such flattened surfaces having a common side which extends axially of the fiber and is centered with respect to the radiation exit region of the optical fiber.

According to further features in the described preferred embodiments, the distal end of the fiber includes an outer radiation-transparent cap in which the visually discernible surface formation is formed.

Further features and advantages of the invention will be apparent from the description below.

The invention is herein described, by way of example only, with reference to the accompanying drawings, wherein:

FIG. 1 pictorially illustrates one form of optical fiber constructed in accordance with the present invention;

FIG. 4 pictorially illustrates a second form of optical fiber constructed in accordance with the present invention;

FIG. 5 is a plan view of the optical fiber of FIG. 4;

FIG. 6 is a side elevational view of the optical fiber of FIG. 4; and

FIG. 7 is a sectional view of the optical fiber of FIGS. 4–6.

Figure 1:
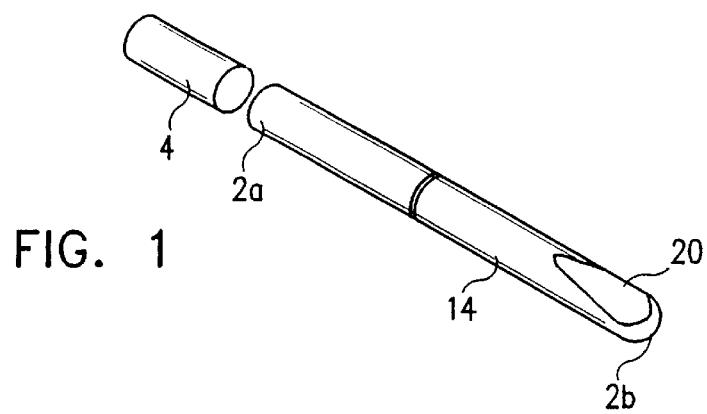
Figure 2:
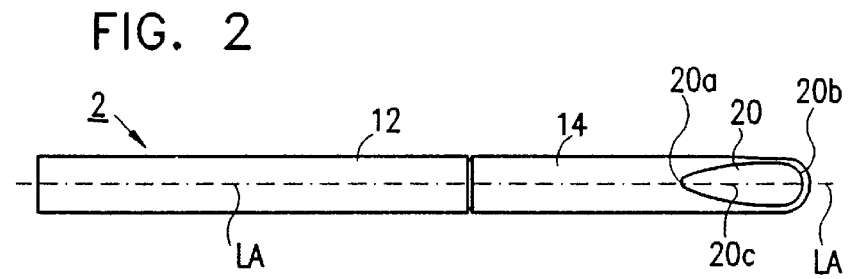
FIG. 2 is a plan view illustrating the optical fiber of FIG. 1.
Figure 3:
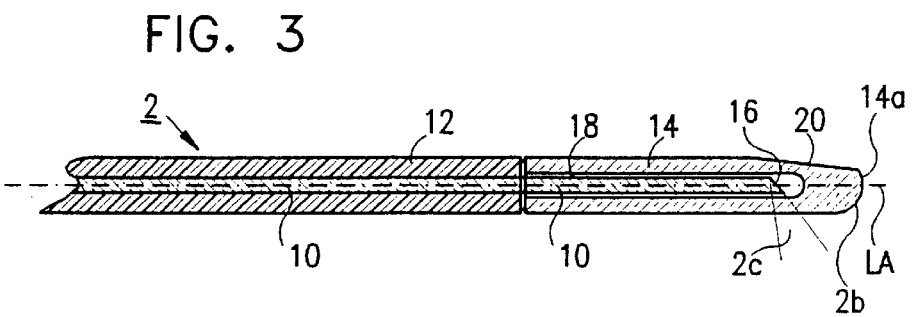
FIG. 3 is a sectional view illustrating the optical fiber of FIGS. 1 and 2.

FIGS. 1–3 illustrate one form of side-emitting (or side-firing) optical fiber, generally designated 2, for use with a laser 4. Fiber 2 includes a proximal end 2a for receiving radiation from the laser 4, and a distal end 2b for emitting the radiation in a direction laterally of the longitudinal axis LA of the fiber via a radiation exit region, shown as 2c in FIG. 3, at the distal end of the fiber.

Fiber 2 illustrated in FIGS. 1–3 may be of any conventional construction. It includes an elongated fiber core 10 which transmits the radiation, and an outer jacket 12 protecting the core and confining the radiation within it. The outer jacket 12, which may be of a known construction constituted of a plurality of plastic layers, terminates at the distal end 2b of the optical fiber. An outer cap 14, preferably of glass, is applied over the core 10 at its distal end. The distal end of the core 10 terminates in an angled reflecting surface 16 effective to reflect the radiation laterally of the longitudinal axis LA of the fiber and through the radiation-transparent glass cap 14, to exit via region 2c shown in FIG. 3.

Glass cap 14 is of cylindrical configuration. It has an inner diameter slightly larger than the outer diameter of the core 10 enclosed by the cap so as to provide an annular air space 18 between the two. Glass cap 14 terminates in a substantially semi-spherical tip 14a, facilitating its insertion into tissue to be examined or treated by the laser radiation.

According to the present invention, the outer surface of the glass cap 14 is formed with a visually discernible surface formation which is narrow at the end thereof facing the proximal end 2a of the fiber 2 and which increases in width towards the end thereof facing the outer tip 14a of the glass cap 14. Such a surface formation thereby enables visually discerning the orientation of the optical fiber with respect to the radiation exit region 2c of the fiber. In the embodiment illustrated in FIGS. 1–3, this visually discernible surface formation is in the form of a substantially flattened surface, shown at 20, which extends at an acute angle to, and towards, the longitudinal axis LA of the fiber in the direction towards the outer tip 14b of the glass cap 14.

Thus, in view of the cylindrical configuration and the hemispherical tip of the glass cap 14 in which flattened surface 20 is formed, and in view of the inclination of the flattened surface with respect to the longitudinal axis LA of the fiber, this flattened surface 20 will take the general form of a tear drop, having a narrow end 20a facing the proximal end 2a of the fiber, and a wide end 20b facing the distal end 2b of the fiber. As shown in FIG. 3, this flattened surface 20 is formed on the face of the glass cap 14 opposite to that through which the radiation is reflected by the angled reflector surface 16. This flattened surface 20 may be produced by holding the optical fiber 2 while pressing its cap 14 against the surface of a grinder wheel or flat grinder disc at an angle to the grinder surface. Flattened surface 20 may thereafter be polished if desired. The longitudinal axis 20c of surface 20 should be aligned with the corresponding axis of the inclined reflector surface 16 of the fiber core 10.

Thus, when using the laser 4 and fiber 2 for radiating tissue, it will be seen that the radiation will be reflected laterally of the fiber by the inclined reflector face 16 of the fiber core and will exit from the fiber laterally via the radiation exit region 2c as illustrated in FIG. 3. Since the longitudinal axis 20c of the flattened surface 20 is always in alignment with the radiation exit region 2c, but on the opposite side of the glass cap 14, the surgeon by viewing this flattened surface can continuously visually discern the orientation of the optical fiber with respect to the radiation exit region 2c.

In addition, since the dimensions of the flattened surface 20 are known beforehand, this surface can also provide the surgeon with an indication of the depth of penetration of the distal end of the fiber into the tissue being treated, or an indication of the size of certain tissue at the working site.

FIGS. 4–7 illustrate an optical fiber construction similar to that of FIGS. 1–3, except that instead of providing the distal end of the fiber with a single flattened surface (20), the end of the fiber in FIGS. 4–6 is provided with two such flattened surfaces, shown at 21 and 22, respectively, in contiguous relation to each other and at a slight angle to each other such that they have a common side 23 between them. In this case, the common side 23 is aligned with the longitudinal axis through the angled reflective surface 16 at the end of the fiber core 10. Thus, this viewable common side 23 extends substantially linearly along the length of the glass cap 14, from its distal tip 14a, and thereby provides a clear indication of the axis of the radiation exit region 2c.

In substantially all other respects, the optical fiber illustrated in FIGS. 4–7 is constructed and operates in substantially the same manner as described above with respect to FIGS. 1–3.

The double-flat surfaces formed in the optical fiber of FIGS. 4–7 provides an even more sharper visual indication to the surgeon as to the orientation of the direction from which the laser radiation exits from the fiber. Since the dimensions of the double-flat surface configuration in this embodiment are also known beforehand, and since the outer sides of this formation also taper towards each other from the distal tip of the glass cap to a point inwardly of the glass cap, it will be seen that this construction also provides an indication to the surgeon, not only of the orientation of the glass with respect to the radiation exit region, but also an indication of the depth of penetration of the tip fiber into tissue, and further, an indication of the size of tissue at the working site of the fiber.

While the invention has been described with respect to two preferred embodiments, it will be appreciated that these are set forth merely for purposes of example, and that many other variations, modifications and applications of the invention may be made.

I claim:

1. A side-emitting optical fiber that has a longitudinal axis in a direction of elongation comprising a proximal end for receiving radiation and a distal end for emitting the radiation via a radiation exit region at said distal end; the distal end having an outer surface formed with a visually discernible surface formation that defines a configuration that is elongated in the direction of elongation of the fiber and that increasingly narrows in dimension toward one of the ends to thereby enable visually discerning the orientation of the optical fiber with respect to the radiation exit region thereof the configuration having a maximum width transverse to the direction of elongation that is substantially smaller than a diameter of the fiber.

2. The optical fiber according to claim 1, wherein said visually discernible surface formation is on a side of said optical fiber distal and opposite to said radiation exit region thereof and in alignment therewith.

3. Laser apparatus including a laser emitting laser radiation, and an optical fiber according to claim 1 located such that said proximal end receives the laser radiation emitted by the laser and emits such radiation via said radiation exit region at the distal end of the optical fiber.

4. The optical fiber according to claim 1, further comprising a fiber core extending along said longitudinal axis and having an inclined reflector face that faces said visually discernable surface formation.

5. The optical fiber according to claim 1, wherein said configuration is inclined in the direction of elongation relative to said longitudinal axis.

6. The optical fiber according to claim 1, wherein said discernible surface formation is narrow at the end thereof facing the proximal end of the fiber, and increases in width towards the end thereof facing the distal end of the fiber.

7. The optical fiber according to claim 6, wherein said visually discernible surface formation is on a side of said optical fiber distal and opposite to said radiation exit region thereof and in alignment therewith.

8. The optical fiber according to claim 6, wherein the outer surface of the distal end of the fiber is substantially of cylindrical configuration and terminates in a substantially hemispherical outer tip, and said visually discernable surface formation including a substantially flattened surface extending at an acute angle to the longitudinal axis of the fiber from the outer tip to a location spaced from the outer tip.

9. The optical fiber according to claim 8, wherein said distal end of the fiber includes an outer radiation-transparent cap in which said visually discernible surface formation is formed.

10. The optical fiber according to claim 8, wherein said flattened surface is aligned with said radiation exit region of the distal end of the optical fiber.

11. The optical fiber according to claim 8, wherein said visually discernible surface formation includes two of said substantially flattened surfaces having a common side extending longitudinally of the fiber and centered with respect to said radiation exit region thereof.

12. The optical fiber according to claim 8, wherein each of said substantially flattened surfaces is a polished flattened surface.

13. The optical fiber according to claim 4, wherein each of said substantially flattened surfaces is a polished flattened surface.

14. The optical fiber according to claim 8, wherein said visually discernible surface formation is on a side of said optical fiber distal and opposite to said radiation exit region thereof and in alignment therewith.

15. The optical fiber according to claim 1, wherein said distal end of the fiber includes an outer radiation-transparent cap in which said visually discernible surface formation is formed.

16. The optical fiber according to claim 15, wherein said outer cap includes glass.

17. The optical fiber according to claim 16, wherein the fiber includes an elongated core terminating at the distal end of the fiber in an angled reflecting surface effective to emit the radiation laterally of the longitudinal axis of the fiber via said radiation exit region.

18. The optical fiber according to claim 6, wherein said distal end of the fiber includes an outer radiation-transparent cap in which said visually discernible surface formation is formed.

19. The optical fiber according to claim 18, wherein said outer cap includes glass.

20. The optical fiber according to claim 15, wherein the fiber includes an elongated core terminating at the distal end of the fiber in an angled reflecting surface effective to emit the radiation laterally of the longitudinal axis of the fiber via said radiation exit region.

21. The optical fiber according to claim 20, wherein said fiber further includes an outer jacket enclosing said elongated core and terminating at the distal end of the fiber substantially flush with said radiation-transparent cap.

22. Laser apparatus including a laser emitting laser radiation, and an optical fiber according to claim 6 located such that said proximal end receives the laser radiation emitted by the laser and emits such radiation via said radiation exit region at the distal end of the optical fiber.

* * * * *